United States Patent
Wikiel et al.

(10) Patent No.: US 9,864,345 B2
(45) Date of Patent: Jan. 9, 2018

(54) ELIMINATING TEMPERATURE VARIATION EFFECTS TO IMPROVE ACCURACY OF ELECTROPLATING BATH MONITORING

(71) Applicant: TECHNIC, INC., Cranston, RI (US)

(72) Inventors: Kazimierz Wikiel, Wakefield, RI (US); Aleksander Jaworski, Franklin, MA (US); Wojciech Wikiel, Cranston, RI (US)

(73) Assignee: TECHNIC, INC., Cranston, RI (US)

( * ) Notice: Subject to any disclaimer, the term of this patent is extended or adjusted under 35 U.S.C. 154(b) by 513 days.

(21) Appl. No.: 14/574,454

(22) Filed: Dec. 18, 2014

(65) Prior Publication Data
US 2015/0220851 A1 Aug. 6, 2015

Related U.S. Application Data

(60) Provisional application No. 61/934,013, filed on Jan. 31, 2014.

(51) Int. Cl.
*G01N 27/42* (2006.01)
*G05B 13/00* (2006.01)
(Continued)

(52) U.S. Cl.
CPC .......... *G05B 13/00* (2013.01); *G01N 27/416* (2013.01); *G01N 27/48* (2013.01); *G01N 27/42* (2013.01); *G01N 33/20* (2013.01)

(58) Field of Classification Search
CPC ....... G01N 27/48; G01N 27/416; G01N 33/20
See application file for complete search history.

(56) References Cited

U.S. PATENT DOCUMENTS 4,146,437 A * 3/1979 O'Keefe .............. G01N 27/48
204/412
7,270,733 B2 * 9/2007 Wikiel .................. G01N 27/42
205/775
(Continued)

OTHER PUBLICATIONS

Yokogawa Technical Note, pH Temperature Compensation, TNA0924 (May 13, 2009) available at: cdn2.us.yokogawa.com/TNA0924.pdf.
(Continued)

*Primary Examiner* — Alexander Noguerola
(74) *Attorney, Agent, or Firm* — Chace Ruttenberg & Freedman LLP

(57) ABSTRACT

A process for creating a predictive data set predicting the amount of target constituents are in an electrolyte solution at varying temperatures is provided. The process includes (a) obtaining a sample set in which each sample comprises an electrolyte solution of known composition; (b) obtaining an electroanalytical response for each sample in the sample set to produce a electroanalytical response data set at a pre-determined, chosen target temperature; (c) obtaining a plurality of training sets, each training set being measured at a different pre-selected temperature in a range of low to high temperatures that comprises the sample set and corresponds to the electroanalytical response data set; (d) analyzing each of the training sets individually using decomposition and multivariate regression methods to produce a plurality of regression data sets, each at different temperature; and (e) validating the plurality of training data sets to produce a predictive data set for predictive calibration models, each at different temperatures in the pre-selected range of low to high temperatures.

17 Claims, 5 Drawing Sheets

(51) Int. Cl.
    *G01N 27/48*     (2006.01)
    *G01N 27/416*     (2006.01)
    *G01N 33/20*     (2006.01)

(56) References Cited

U.S. PATENT DOCUMENTS 7,781,222 B2     8/2010   Wu
2004/0055888 A1*   3/2004   Wikiel ................ C23C 18/1683
                                                                205/81

OTHER PUBLICATIONS

Gray, DM and Bevilacqua, AC, Cation Conductivity Temperature Compensation, Proc. International Water Conference, Pittsburg, PA (1997).

Nakagomi, Sai and Kokubun, Sensors and Actuators, B187, p. 413 (2013).

Wulfert, Kok and Smilde, Influence of Temperature on Vibrational Spectra and Consequences for the Predictive Ability of Multivariate Models, Anan. Chem. 70 (1998) 1761.

Haaland, DM, Synthetic Multivariate Models to Accomodate Unmodeled Interfering Spectral Components during Quantitative Spectral Analysis, Appl. Spectrosc. 54, (2000) 246.

Wang, Y and Kowalski, BR, Temperature-Compensating Calibration Transfer for Near-Infrared Filter Instruments, Anal. Chem. 65 (1993) 1301.

Wulfert, Kok, De Noord and Smilde, Correction of Temperature-Induced Spectral Variation by Continuous Piecewise Direct Standardization, Anal. Chem. 72 (2000) 1639.

Chen, Morris and Martin, Correction of Temperature-Induced Spectral Variations by Loading Space Standardization, Anal. Chem. 77 (2005) 1376.

Morash, Thornton, Saunders Bevilacqua and Light, Measurement of the Resistivity of Ultrapure Water at Elevated Temperatures, Ultrapure Water Journal, Dec. 18, 1994.

\* cited by examiner

ELIMINATING TEMPERATURE VARIATION EFFECTS TO IMPROVE ACCURACY OF ELECTROPLATING BATH MONITORING

CROSS-REFERENCE TO RELATED APPLICATIONS

This application claims the benefit of Provisional Application Ser. No. 61/934,013, filed Jan. 31, 2014.

FIELD OF THE INVENTION

The invention relates generally to monitoring the performance of electroplating solutions. More specifically, the invention relates to plating baths and methods for monitoring plating functionality based on chemometric analysis of voltammetric data obtained for these baths. Chemometric techniques are applied to build a quantitative calibration model that compensates for temperature variations resulting in improved reliability of plating bath component measurements.

BACKGROUND OF THE INVENTION

Modern electroplating processes are widely used for the manufacturing of semiconductor parts and devices. Being a part of manufacturing of sophisticated and very highly integrated circuits, these processes require rigorous monitoring. One monitoring system, the Real Time Analyzer (RTA (Technic, Inc., Cranston, R.I.) allows control of electroplating solutions to the extent expected in the highly demanding semiconductor manufacturing. The system performs an in-situ analysis using exclusively electroanalytical techniques for the bath constituents.

The advantages of using electroanalytical measurements to monitor and/or control plating bath solutions include direct (as opposed to indirect, requiring sample pretreatment) analysis and non-invasiveness. Such electroanalytical methods perform activities very similar to those performed by the electroplating processes themselves, but at a significantly smaller scale. Thus, these electrochemical/electroanalytical measurements do not introduce any changes into the analyzed solutions, which can be returned to the bath after analysis. Alternatively, the solution after analysis can be directed to the wastes, if returning it back to the bath is not preferred by the process route.

By directly analyzing the undiluted plating bath solution using such electrochemical methods, the RTA approach provides accurate measurements of each added constituent of the bath and can characterize the plating bath performance while the plating is in process, thereby enabling early fault detection to minimize waste.

Because electrochemical processes (electroplating as well as electroanalysis) are sensitive to temperature variations in the electroplating solution, in order to achieve high stability and reliability of electroanalytical measurements (and the electroplating process thereby), the temperature of the measured solutions need to be maintained at constant level within a narrow tolerance range. In other words, the belief is that tight temperature control is required for semiconductor manufacturing and bath analysis.

Two possible designs for a sampling device allowing plating bath analyses with temperature control are presented in FIGS. 1 and 2. (For simplicity, the electrical connection from the probe to the computerized potentiostat is omitted from these figures.)

FIG. 1 illustrates a simple temperature controlled measurement setup with a closed-loop bath circulation. A vessel containing a solution to be analyzed is submersed into a temperature controlled device. The RTA probe (an electrochemical cell used for the measurements) is submersed in the same device. The solution from the bottle is delivered to the probe by a PTFE membrane pump (required by RTA measurement routines). Since the temperature in the measurement compartment (a bottom part of the RTA probe) and the vessel containing a sample of analyzed solution need to be kept at the same temperature, both pieces need to be submersed as much as possible in the constant temperature device. The temperature controlled device can be any of these: a chilling-heating baths (a classical water bath, for example), a closed air chamber, or devices used for technological processes (in this case electroplating) such as a plating solution reservoir tank. This temperature controlled device may comprise very different approaches and may be modified depending on effectiveness, cost and/or simplicity. It is well known that the stability and effectiveness of liquid temperature controlled devices are much higher than air-based or gas-based devices. On the other hand, it is quite difficult to fully submerse the pump and all tubing in such a liquid-based device.

The liquid-based temperature control devices seem to be much more effective, thus more frequently used. Although the exposure of the tubing, pumps and valves can be minimized, it is not simple to eliminate its negative impact totally. This task is getting even more difficult with the extent of automation required by the applications (the simpler the setup, the easier the way of maintaining constant temperature). These complications are shown in FIG. 2, which illustrates a multi-stream capable temperature controlled measurement setup. Having different stream paths delivering different solutions to the sampling vessel and the probe requires several valves, pumps, and associated tubing. What this means is that more parts are exposed to the environment at a different than required temperature. Because these portions of the setup are exposed to the non-temperature controlled environment, additional temperature variations in the analyzed solution may be introduced during the sometimes quite lengthy (typically 15-40 min.) full analysis cycle. On top of these factors, if different streams deliver solution from different sources (bath controlled solution vs. standard solution(s) that usually does not come from temperature-controlled containers), the integrity of the analytical system can be compromised, i.e., analyses of different samples may be performed at different temperatures compromising the robustness of the measurements.

FIGS. 1 and 2 show two possible general layouts as examples. But by an appropriate combination of pumps and valves, any design can be achieved depending on the requirements for the inbound and outbound streams, and the size of sample that is analyzed.

Although the foregoing device designs are feasible, there is an alternative approach that can eliminate all (or almost all) negative effects that are caused by temperature variation in the RTA probe. In U.S. Pat. No. 7,270,733, we disclosed methods for real time monitoring of the constituent electrolytes in electroplating baths based on the chemometric analysis of voltammetric data, specifically using a number of chemometric techniques including modeling power, outlier detection, regression and calibration transfer for analysis of the voltammetric data obtained for various plating baths. Here, we extend these methods to improve robustness and accuracy of analyses by eliminating the effects of varying temperature (during the measurement time) on bath measurements. As a result, the focus of the design is shifted from building a complex, difficult to maintain, and expensive device with a very tight temperature control, to building a software model that allows for compensation of the varying temperature effects.

SUMMARY OF THE INVENTION

U.S. Pat. No. 7,270,733 is herein incorporated by reference for the substance of its disclosure.

The invention is a process for creating a predictive data set for use in predicting the amount of target constituent in an electrolyte solution at varying temperatures. The process includes the steps of (a) obtaining an electrolyte solution sample set, wherein each sample in the set comprises an electrolyte solution of known composition; (b) obtaining an electroanalytical response for each sample in the sample set to produce a electroanalytical response data set at a predetermined, chosen target temperature; (c) obtaining a plurality of training sets, each training set being measured at a different temperature in a range of low to high temperatures that comprises said sample set and corresponds to said electroanalytical response data set; (d) analyzing each of said training sets individually using decomposition and multivariate regression methods to produce a plurality of regression data sets each at different temperature; and (e) validating the plurality of training data sets to produce a predictive data set for predictive calibration models each at different temperatures in the pre-determined, chosen range of low to high temperatures.

The process may be employed with electrolyte solutions in an electroplating bath, particularly an electroplating bath that includes one or more metals selected from copper (Cu), tin (Sn), lead (Pb), zinc (Zn), nickel (Ni), silver (Ag), cadmium (Cd), cobalt (Co), chromium (Cr), and/or their alloys. The process may also be employed with electrolyte solutions in an electroless plating bath, particularly an electroless plating bath that includes an autocatalytic plating bath of one or more metals selected from Cu, Sn, Pb, Ni, Ag, gold (Au), and/or their alloys or an immersion plating bath of one or more metals selected from Cu, Sn, Pb, Ni, Ag, Au and/or their alloys. In another embodiment, the process may be employed with electrolyte solutions in electrowinning baths, electrorefining baths, electromicromachining baths, electroforming baths and electropolishing baths that include one or more metals selected from Cu, Sn, Pb, Zn, Ni, Ag, Cd, Co, Cr, and/or their alloys.

Step (a) of the foregoing process can be obtained using a design of experiment (DOE) routine, such as for example, a multicomponent multilevel fractional factorial.

Step (b) of the foregoing process can be obtained using a DC Scan Voltammetry, DC Anodic Stripping Voltammetry, DC Cathodic Stripping Voltammetry, DC Adsorptive Stripping Voltammetry, and DC Cyclic Voltammetric Stripping. Also, DC Staircase Voltammetry, Normal Pulse Voltammetry, Reverse Pulse Voltammetry, Differential Pulse Voltammetry, Square Wave Voltammetry, AC Voltammetry, Multi-Frequency AC Voltammetry, Chronoamperometry, Chronopotentiometry, Electrochemical Impedance Spectroscopy, Dynamic Electrochemical Impedance Spectroscopy, a Polarographic technique, or a combination of any two or more of the foregoing techniques may be employed. The electroanalytical response obtained in step (b) will comprise a plurality of data points. It may be a combination of one or more portions of a complete electroanalytical response or a combination of one or more portions of independent electroanalytical responses.

Step (d) of the foregoing process can be obtained by sequential decomposition followed by a multivariate regression (PCR, HPCR, CPCR, PARAFAC/ILS) or by simultaneous decomposition and regression (PLS, HPLS, MBPLS, N-PLS).

Step (e) may be accomplished through internal validation and/or external validation. If internal validation is used, the validation will preferably employ cross validation, including the steps of a) omitting a single sample from the training set, thereby creating a new training set; (b) analyzing the new training set using a decomposition and a multivariate regression method to produce a new regression data set; (c) predicting the omitted sample target component concentration using the new regression data set; (d) returning the sample to the training set; (e) repeating steps (a) through (d) until all individual samples are treated; (f) determining an $R^2$ value for the predicted samples based on the predicted and the known concentrations; and (g) validating the training data set if the $R^2$ value is above about 0.95 or repeating steps (a) to (e) if the $R^2$ value is less than about 0.95. If the external validation is used, the procedure consists of the following steps: (a) obtaining a second sample set comprising an electrolyte solution of known composition, (b) obtaining an electroanalytical response for each sample of the second sample set, (c) predicting the target component concentration for each sample of the second sample set using the predictive calibration model, (d) determining an $R^2$ value for all samples of said second sample set based on said predicted and said known concentrations and (e) validating the predictive calibration model if the $R^2$ value is above about 0.95. If the said $R^2$ value is less than about 0.95, then steps (a) to (e) are repeated until the value is above about 0.95.

In another embodiment, the invention includes a process of creating a calibration data set to predict the amount of a target constituent in an electrolyte solution at various temperatures. In this embodiment the process includes the steps of (a) obtaining a sample set, wherein each sample in the set comprises an electrolyte solution of known composition, (b) obtaining an electroanalytical response for each sample in the sample set to produce an electroanalytical response data set at a target temperature and at various temperatures in a pre-selected range of low to high temperature limits, (c) obtaining a training set that comprises the sample set and the corresponding electroanalytical response data set at various temperatures in the pre-selected range of low to high temperature limits including the target temperature, (d) preprocessing the training set, (e) determining the calibration range, (f) detecting and eliminating outliers from the response data set, (g) determining the optimal number of factors (h) detecting and eliminating outliers within training set, (i) analyzing the training set using multivariate regression to produce a regression set at the target temperature, (j) analyzing a subset of the training using multivariate regression to compensate for the temperature effect to produce a regression set with temperature compensation, and (k) validating the regression set with temperature compensation to produce a predictive set for a predictive calibration model for various temperatures in the pre-selected range low to high limits.

This process also may be employed with electrolyte solutions in an electroplating bath, particularly an electroplating bath that includes one or more metals selected from copper (Cu), tin (Sn), lead (Pb), zinc (Zn), nickel (Ni), silver (Ag), cadmium (Cd), cobalt (Co), chromium (Cr), and/or their alloys. The process may also be employed with electrolyte solutions in an electroless plating bath, particularly an electroless plating bath that includes an autocatalytic plating bath of one or more metals selected from Cu, Sn, Pb, Ni, Ag, gold (Au), and/or their alloys or an immersion plating bath of one or more metals selected from Cu, Sn, Pb, Ni, Ag, Au and/or their alloys. In another embodiment, the process may be employed with electrolyte solutions in electrowinning baths, electrorefining baths, electromicromachining baths, electroforming baths and electropolishing baths that include one or more metals selected from Cu, Sn, Pb, Zn, Ni, Ag, Cd, Co, Cr, and/or their alloys.

Step (a) of the foregoing process can be obtained using a design of experiment (DOE) routine, such as for example, a multicomponent multilevel linear orthogonal array or a multicomponent multilevel fractional factorial.

As in the first process, step (b) of the foregoing process can be obtained using a DC Voltammetry technique, such as for example DC Cyclic Voltammetry, DC Linear Scan Voltammetry, DC Anodic Stripping Voltammetry, DC Cathodic Stripping Voltammetry, DC Adsorptive Stripping Voltammetry, and DC Cyclic Voltammetric Stripping. Also, DC Staircase Voltammetry, Normal Pulse Voltammetry, Reverse Pulse Voltammetry, Differential Pulse Voltammetry, Square Wave Voltammetry, AC Voltammetry, Multi-Frequency AC Voltammetry, Chronoamperometry, Chronopotentiometry, Electrochemical Impedance Spectroscopy, Dynamic Electrochemical Impedance Spectroscopy, a Polarographic technique, or a combination of any two or more of the foregoing techniques may be employed. The electroanalytical response obtained in step (b) will comprise a plurality of data points. It may be a combination of one or more portions of a complete electroanalytical response or a combination of one or more portions of independent electroanalytical responses.

Step (d) of the foregoing process includes autoscaling the data to unit variance, i.e., performing mean centering and dividing by the standard deviation.

Step (e) of the foregoing process includes analyzing the data using correlation coefficient calculations based on the least squares regression, using SIMCA based calculations of modeling power and using a product of the correlation coefficient and the modeling power.

Step (f) of the foregoing process is accomplished by analyzing the data using one of the following: principle component analysis, Mahalanobis distance, Mahalanobis distance coupled with principal component analysis, Mahalanobis distance coupled with the principal component analysis with Q residuals, SIMCA, or PRESS. If PRESS is used, the analysis is based on PCR, HPCR, CPCR, PARAFAC/ILS calculations or on PLS, HPLS, MBPLS, N-PLS calculations.

Step (g) of the foregoing process is accomplished by analyzing the data using Exner psi function calculations, which can be based on PCR, HPCR, CPCR, PARAFAC/ILS calculations or on PLS, HPLS, MBPLS, N-PLS calculations.

Step (h) of the foregoing process is accomplished by analyzing the data using F sup. C-ratio analysis, Studentized concentration residuals analysis, leverages analysis, or Studentized concentration residuals analysis coupled with leverages analysis.

Step (i) is accomplished by analyzing the data using PLS, HPLS, MBPLS, N-PLS or using PCR, HPCR, CPCR, PARAFAC/ILS.

Validation step (j) is accomplished through internal validation and external validation. Internal validation uses cross validation, which includes omitting a single sample from the training set, thereby creating a new training set, analyzing the new training set using decomposition and multivariate regression methods to produce a new regression data set, predicting the omitted sample target component concentration using the new regression data set, returning the sample to the training set, and repeating these steps until all individual samples are treated. Next an $R^2$ value for the predicted samples based on the predicted and the known concentrations is determined. If the $R^2$ value is above about 0.95, the validation is complete. If the $R^2$ value is less than about 0.95, the steps are repeated until the $R^2$ value is above about 0.95.

DETAILED DESCRIPTION OF THE INVENTION

Figure 1:
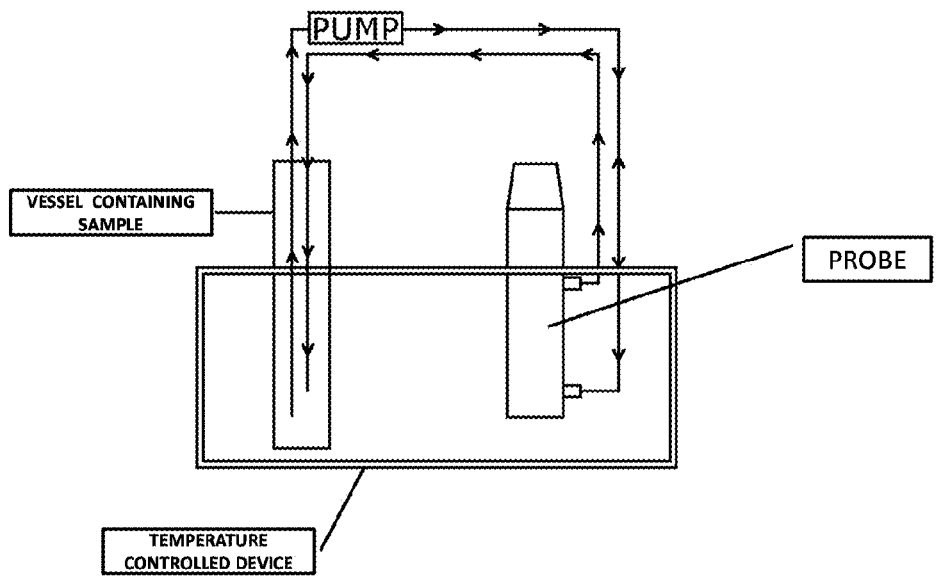
FIG. 1 is an illustration of one possible way to maintain and control constant temperature of a bath sample in a simple sampling device.
Figure 2:
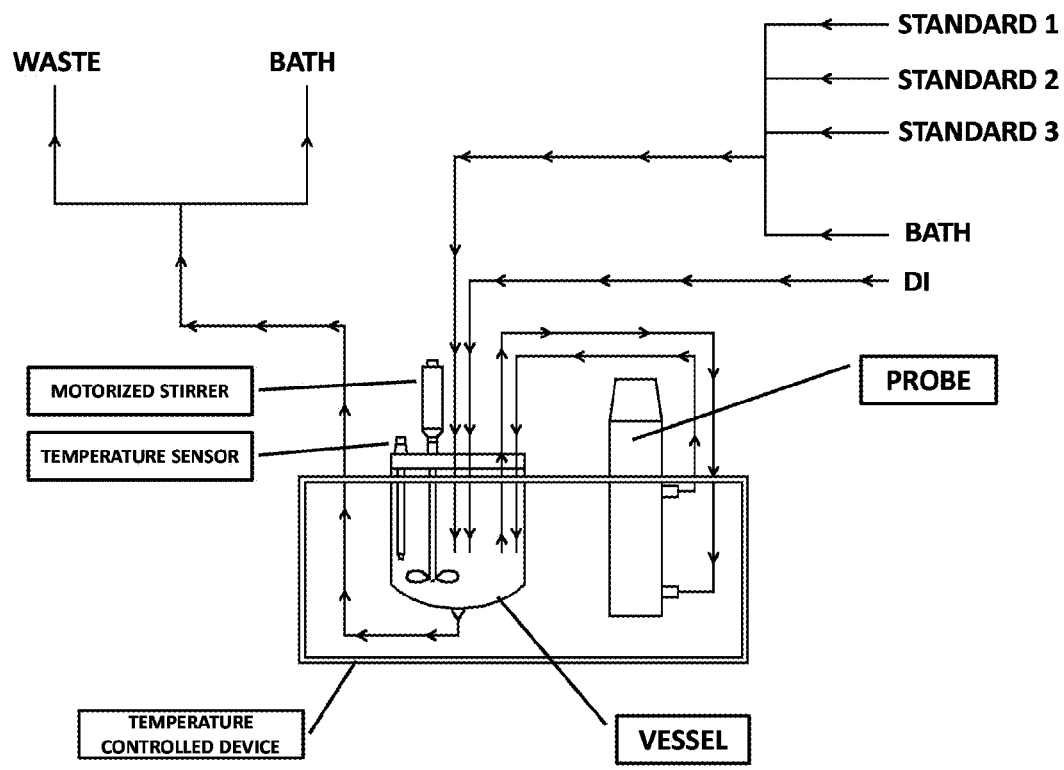
FIG. 2 is an illustration of a second possible way to maintain and control constant temperature of a bath sample in a more complex sampling device. For clarity, all necessary pumps and valves are not shown.

Two methods utilizing temperature compensation are presented in greater detail. Although they have some initial steps in common, they differ from each other enough to be described separately. The first method consists of two distinctive steps, in that master calibration is performed at the constant temperature followed by a separate temperature study and temperature compensation calculation. Each of these steps requires separate regression calculations. Therefore, it is a dual-regression method. In the second method, the temperature variation is already embedded in the master calibration resulting in a single regression model referred to herein as an embedded temperature method.

The performance of each method is illustrated by different examples of actual plating baths differing from each other both qualitatively and quantitatively. However, both presented methods are universal, not bath-specific.

Formalism

The baths used for introduction and illustration of both temperature compensation methods consist of K=6 deliberately added bath constituents indexed k=1, . . . , K. The concentration of bath constituents vary within calibration ranges symmetrically around the corresponding target concentration. For instance, for k-th component the concentration range is following $(c_{i,T} - \Delta c_i; c_{i,T} + \Delta c_i)$, where c denotes concentration and subscript T denotes target level. The analytical model should be capable of compensating the temperature fluctuations within the range $(T_T-\Delta T; T_T+\Delta T)$ where T denotes the temperature.

The voltammetric data for one analysis is used for determination of concentrations of all deliberately added bath constituents. The voltammetric data for one analysis consists of a sequence of various voltammograms, differing in their waveforms. The k-th component can be analyzed using l=1, ..., L different voltammograms (of different waveforms). The execution of voltammogram of l-th waveform for k-th component can be repeated m=1, ..., M times during the different portions of the sequence of voltammograms. The temperature compensation is implemented individually for each m-th voltammogram of l-th waveform to calculate the predicted concentrations of k-th component. These predicted concentrations are averaged and the resultant predicted concentration of k-th component is reported. This individual temperature compensation is based on concurrent-to-electroanalysis, continuous temperature monitoring. Therefore, each individual analysis is independently and individually temperature compensated.

Matrices are symbolized by bolded capital letters, while vectors are bolded lower script letters. The elements of a vector are denoted with the same lower case letter as the vector but not bolded.

The subscripts Supp, Acc, and Lev denote any suppressor, accelerator, and leveler, respectively. These descriptions do not refer to organic constituents of specific plating bath, but are general and cover entire category of organic additives for all applicable baths. Therefore, although different (both qualitatively and quantitatively) baths are used for illustrating application of both temperature compensation methods, their organic constituents are referred to commonly as Supp, Acc, and Lev.

Approach 1: Dual-Regression Method

Step 1-1: Waveform Development

The waveform development is an iterative selection and optimization of parameters of voltammetric waveforms to obtain signals whose portions are linearly dependent on changing concentrations of a k-th component of interest while being independent of changing concentration of all other bath constituents. For each k-th component various L waveforms can meet these criteria. Several (L) waveforms are included in the analytical model as they analyze the component of interest from different physicochemical perspective. Also, the same waveforms can be repeated M times in the different portions of the sequence of scans during one analysis. The solutions used for waveform development are composed based on the 2-level, 6-component fractional factorial resulting in 8 different concentration combinations. An additional, ninth solution is of Target level composition for all bath constituents. The measurements are conducted at the target temperature (see Table 1).

TABLE 1

Waveform Development Training Set

| Sol # | Copper | Acid | Chloride | Suppressor | Accelerator | Leveler |
|---|---|---|---|---|---|---|
| D1 | $c_{Cu,T} - \Delta c_{Cu}$ | $c_{Acid,T} - \Delta c_{Acid}$ | $c_{Cl,T} - \Delta c_{Cl}$ | $c_{Supp,T} + \Delta c_{Supp}$ | $c_{Acc,T} + \Delta c_{Acc}$ | $c_{Lev,T} + \Delta c_{Lev}$ |
| D2 | $c_{Cu,T} + \Delta c_{Cu}$ | $c_{Acid,T} - \Delta c_{Acid}$ | $c_{Cl,T} - \Delta c_{Cl}$ | $c_{Supp,T} - \Delta c_{Supp}$ | $c_{Acc,T} - \Delta c_{Acc}$ | $c_{Lev,T} + \Delta c_{Lev}$ |
| D3 | $c_{Cu,T} - \Delta c_{Cu}$ | $c_{Acid,T} + \Delta c_{Acid}$ | $c_{Cl,T} - \Delta c_{Cl}$ | $c_{Supp,T} - \Delta c_{Supp}$ | $c_{Acc,T} + \Delta c_{Acc}$ | $c_{Lev,T} - \Delta c_{Lev}$ |
| D4 | $c_{Cu,T} + \Delta c_{Cu}$ | $c_{Acid,T} + \Delta c_{Acid}$ | $c_{Cl,T} - \Delta c_{Cl}$ | $c_{Supp,T} + \Delta c_{Supp}$ | $c_{Acc,T} - \Delta c_{Acc}$ | $c_{Lev,T} - \Delta c_{Lev}$ |
| D5 | $c_{Cu,T} - \Delta c_{Cu}$ | $c_{Acid,T} - \Delta c_{Acid}$ | $c_{Cl,T} + \Delta c_{Cl}$ | $c_{Supp,T} + \Delta c_{Supp}$ | $c_{Acc,T} - \Delta c_{Acc}$ | $c_{Lev,T} - \Delta c_{Lev}$ |
| D6 | $c_{Cu,T} + \Delta c_{Cu}$ | $c_{Acid,T} - \Delta c_{Acid}$ | $c_{Cl,T} + \Delta c_{Cl}$ | $c_{Supp,T} - \Delta c_{Supp}$ | $c_{Acc,T} + \Delta c_{Acc}$ | $c_{Lev,T} - \Delta c_{Lev}$ |
| D7 | $c_{Cu,T} - \Delta c_{Cu}$ | $c_{Acid,T} + \Delta c_{Acid}$ | $c_{Cl,T} + \Delta c_{Cl}$ | $c_{Supp,T} - \Delta c_{Supp}$ | $c_{Acc,T} - \Delta c_{Acc}$ | $c_{Lev,T} + \Delta c_{Lev}$ |
| D8 | $c_{Cu,T} + \Delta c_{Cu}$ | $c_{Acid,T} + \Delta c_{Acid}$ | $c_{Cl,T} + \Delta c_{Cl}$ | $c_{Supp,T} + \Delta c_{Supp}$ | $c_{Acc,T} + \Delta c_{Acc}$ | $c_{Lev,T} + \Delta c_{Lev}$ |
| D9 | $c_{Cu,T}$ | $c_{Acid,T}$ | $c_{Cl,T}$ | $c_{Supp,T}$ | $c_{Acc,T}$ | $C_{Lev,T}$ |

Step 1-2: Master Calibration Training Set

Voltammograms of waveforms developed in Step 1-1 are taken for collection of master calibration training set data, by analyzing 25 solutions composed as a five-level, six-component linear orthogonal array at target temperature. See Table 2.

TABLE 2

Master Calibration Training Set

| Sol # | Copper | Acid | Chloride | Suppressor | Accelerator | Leveler |
|---|---|---|---|---|---|---|
| C1 | $c_{Cu,T} - \Delta c_{Cu}$ | $c_{Acid,T} - \Delta c_{Acid}$ | $c_{Cl,T} - \Delta c_{Cl}$ | $c_{Supp,T} - \Delta c_{Supp}$ | $c_{Acc,T} - \Delta c_{Acc}$ | $c_{Lev,T} - \Delta c_{Lev}$ |
| C2 | $c_{Cu,T} - \Delta c_{Cu}$ | $c_{Acid,T} - 0.5\Delta c_{Acid}$ | $c_{Cl,T} - 0.5\Delta c_{Cl}$ | $c_{Supp,T} - 0.5\Delta c_{Supp}$ | $c_{Acc,T} - 0.5\Delta c_{Acc}$ | $c_{Lev,T} - 0.5\Delta c_{Lev}$ |
| C3 | $c_{Cu,T} - \Delta c_{Cu}$ | $c_{Acid,T}$ | $c_{Cl,T}$ | $c_{Supp,T}$ | $c_{Acc,T}$ | $c_{Lev,T}$ |
| C4 | $c_{Cu,T} - \Delta c_{Cu}$ | $c_{Acid,T} + 0.5\Delta c_{Acid}$ | $c_{Cl,T} + 0.5\Delta c_{Cl}$ | $c_{Supp,T} + 0.5\Delta c_{Supp}$ | $c_{Acc,T} + 0.5\Delta c_{Acc}$ | $c_{Lev,T} + 0.5\Delta c_{Lev}$ |
| C5 | $c_{Cu,T} - \Delta c_{Cu}$ | $c_{Acid,T} + \Delta c_{Acid}$ | $c_{Cl,T} + \Delta c_{Cl}$ | $c_{Supp,T} + \Delta c_{Supp}$ | $c_{Acc,T} + \Delta c_{Acc}$ | $c_{Lev,T} + \Delta c_{Lev}$ |
| C6 | $c_{Cu,T} - 0.5\Delta c_{Cu}$ | $c_{Acid,T} - \Delta c_{Acid}$ | $c_{Cl,T} - 0.5\Delta c_{Cl}$ | $c_{Supp,T}$ | $c_{Acc,T} + 0.5\Delta c_{Acc}$ | $c_{Lev,T} + \Delta c_{Lev}$ |
| C7 | $c_{Cu,T} - 0.5\Delta c_{Cu}$ | $c_{Acid,T} - 0.5\Delta c_{Acid}$ | $c_{Cl,T}$ | $c_{Supp,T} + 0.5\Delta c_{Supp}$ | $c_{Acc,T} + \Delta c_{Acc}$ | $c_{Lev,T} - \Delta c_{Lev}$ |
| C8 | $c_{Cu,T} - 0.5\Delta c_{Cu}$ | $c_{Acid,T}$ | $c_{Cl,T} + 0.5\Delta c_{Cl}$ | $c_{Supp,T} + \Delta c_{Supp}$ | $c_{Acc,T} - \Delta c_{Acc}$ | $c_{Lev,T} - 0.5\Delta c_{Lev}$ |
| C9 | $c_{Cu,T} - 0.5\Delta c_{Cu}$ | $c_{Acid,T} + 0.5\Delta c_{Acid}$ | $c_{Cl,T} + \Delta c_{Cl}$ | $c_{Supp,T} - \Delta c_{Supp}$ | $c_{Acc,T} - 0.5\Delta c_{Acc}$ | $c_{Lev,T}$ |
| C10 | $c_{Cu,T} - 0.5\Delta c_{Cu}$ | $c_{Acid,T} + \Delta c_{Acid}$ | $c_{Cl,T} - \Delta c_{Cl}$ | $c_{Supp,T} - 0.5\Delta c_{Supp}$ | $c_{Acc,T}$ | $c_{Lev,T} + 0.5\Delta c_{Lev}$ |
| C11 | $c_{Cu,T}$ | $c_{Acid,T} - \Delta c_{Acid}$ | $c_{Cl,T}$ | $c_{Supp,T} + \Delta c_{Supp}$ | $c_{Acc,T} - 0.5\Delta c_{Acc}$ | $c_{Lev,T} + 0.5\Delta c_{Lev}$ |
| C12 | $c_{Cu,T}$ | $c_{Acid,T} - 0.5\Delta c_{Acid}$ | $c_{Cl,T} + 0.5\Delta c_{Cl}$ | $c_{Supp,T} - \Delta c_{Supp}$ | $c_{Acc,T}$ | $c_{Lev,T} + \Delta c_{Lev}$ |
| C13 | $c_{Cu,T}$ | $c_{Acid,T}$ | $c_{Cl,T} + \Delta c_{Cl}$ | $c_{Supp,T} - 0.5\Delta c_{Supp}$ | $c_{Acc,T} + 0.5\Delta c_{Acc}$ | $c_{Lev,T} - \Delta c_{Lev}$ |
| C14 | $c_{Cu,T}$ | $c_{Acid,T} + 0.5\Delta c_{Acid}$ | $c_{Cl,T} - \Delta c_{Cl}$ | $c_{Supp,T}$ | $c_{Acc,T} + \Delta c_{Acc}$ | $c_{Lev,T} - 0.5\Delta c_{Lev}$ |
| C15 | $c_{Cu,T}$ | $c_{Acid,T} + \Delta c_{Acid}$ | $c_{Cl,T} - 0.5\Delta c_{Cl}$ | $c_{Supp,T} + 0.5\Delta c_{Supp}$ | $c_{Acc,T} - \Delta c_{Acc}$ | $c_{Lev,T}$ |
| C16 | $c_{Cu,T} + 0.5\Delta c_{Cu}$ | $c_{Acid,T} - \Delta c_{Acid}$ | $c_{Cl,T} + 0.5\Delta c_{Cl}$ | $c_{Supp,T} - 0.5\Delta c_{Supp}$ | $c_{Acc,T} + \Delta c_{Acc}$ | $c_{Lev,T}$ |

TABLE 2-continued

Master Calibration Training Set

| Sol # | Copper | Acid | Chloride | Suppressor | Accelerator | Leveler |
|---|---|---|---|---|---|---|
| C17 | $c_{Cu,\,T} + 0.5\Delta c_{Cu}$ | $c_{Acid,\,T} - 0.5\Delta c_{Acid}$ | $c_{Cl,\,T} + \Delta c_{Cl}$ | $c_{Supp,\,T}$ | $c_{Acc,\,T} - \Delta c_{Acc}$ | $c_{Lev,\,T} + 0.5\Delta c_{Lev}$ |
| C18 | $c_{Cu,\,T} + 0.5\Delta c_{Cu}$ | $c_{Acid,\,T}$ | $c_{Cl,\,T} - \Delta c_{Cl}$ | $c_{Supp,\,T} + 0.5\Delta c_{Supp}$ | $c_{Acc,\,T} - 0.5\Delta c_{Acc}$ | $c_{Lev,\,T} + \Delta c_{Lev}$ |
| C19 | $c_{Cu,\,T} + 0.5\Delta c_{Cu}$ | $c_{Acid,\,T} + 0.5\Delta c_{Acid}$ | $c_{Cl,\,T} - 0.5\Delta c_{Cl}$ | $c_{Supp,\,T} + \Delta c_{Supp}$ | $c_{Acc,\,T}$ | $c_{Lev,\,T} - \Delta c_{Lev}$ |
| C20 | $c_{Cu,\,T} + 0.5\Delta c_{Cu}$ | $c_{Acid,\,T} + \Delta c_{Acid}$ | $c_{Cl,\,T}$ | $c_{Supp,\,T} - \Delta c_{Supp}$ | $c_{Acc,\,T} + 0.5\Delta c_{Acc}$ | $c_{Lev,\,T} - 0.5\Delta c_{Lev}$ |
| C21 | $c_{Cu,\,T} + \Delta c_{Cu}$ | $c_{Acid,\,T} - \Delta c_{Acid}$ | $c_{Cl,\,T} + \Delta c_{Cl}$ | $c_{Supp,\,T} + 0.5\Delta c_{Supp}$ | $c_{Acc,\,T}$ | $c_{Lev,\,T} - 0.5\Delta c_{Lev}$ |
| C22 | $c_{Cu,\,T} + \Delta c_{Cu}$ | $c_{Acid,\,T} - 0.5\Delta c_{Acid}$ | $c_{Cl,\,T} - \Delta c_{Cl}$ | $c_{Supp,\,T} + \Delta c_{Supp}$ | $c_{Acc,\,T} + 0.5\Delta c_{Acc}$ | $c_{Lev,\,T}$ |
| C23 | $c_{Cu,\,T} + \Delta c_{Cu}$ | $c_{Acid,\,T}$ | $c_{Cl,\,T} - 0.5\Delta c_{Cl}$ | $c_{Supp,\,T} - \Delta c_{Supp}$ | $c_{Acc,\,T} + \Delta c_{Acc}$ | $CC_{Lev,\,T} + 0.5\Delta c_{Lev}$ |
| C24 | $c_{Cu,\,T} + \Delta c_{Cu}$ | $c_{Acid,\,T} + 0.5\Delta c_{Acid}$ | $c_{Cl,\,T}$ | $c_{Supp,\,T} - 0.5\Delta c_{Supp}$ | $c_{Acc,\,T} - \Delta c_{Acc}$ | $c_{Lev,\,T} + \Delta c_{Lev}$ |
| C25 | $c_{Cu,\,T} + \Delta c_{Cu}$ | $c_{Acid,\,T} + \Delta c_{Acid}$ | $c_{Cl,\,T} + 0.5\Delta c_{Cl}$ | $c_{Supp,\,T}$ | $c_{Acc,\,T} - 0.5\Delta c_{Acc}$ | $c_{Lev,\,T} - \Delta c_{Lev}$ |

Step 1-3: Initial Regression Calculation

The regression is calculated for a portion of each l-th waveform for k-th component using pretreated by autoscaling voltammetric data. The initial step is the PCA decomposition:

$$X_{k,l} = S_{k,l} V_{k,l}^T + E_{k,l} \quad (1)$$

Where X, S, V, and E are matrices of autoscaled (mean-centering followed by scaling to unit variance within training set) voltammetric data, scores, loads, and residuals, respectively. The superscript T denotes transposed matrix. The voltammetric data of X is a matrix which consists of N rows of J columns, where N is the number of samples recorded for the master calibration training set and J is the number of variables (points of voltammogram) selected for l-th waveform to be used for calibration of k-th bath constituent. The matrix X of dimensions (N×J) is decomposed by F factors, therefore the dimensions of matrices S, V and E are following: (N×F), (J×F) and (N×J), respectively.

The matrix of scores is regressed linearly against the vector of concentrations by means of Inverse Least Squares (ILS). For each k-th component and l-th waveform the corresponding vector of F regression equation coefficients is calculated:

$$\beta_{k,l} = (S_{k,l}^T S_{k,l})^{-1} S_{k,l}^T c_k \quad (2)$$

Step 1-4: Temperature Compensation Calculation by Second Regression

The dependence of concentration readings on temperature for each of k-th components for each of the l-th waveforms is determined by the least squares minimization of the following equation:

$$c_{k,l,T-T_T} = c_{k,l,T_T} + b_{k,l}(T - T_T) \quad (3)$$

To obtain the following slope:

$$b_{k,l} = \frac{\sum_{i=1}^{I} c_{k,l,T_i-T_T}(T_i - T_T) - \frac{1}{I}\sum_{i=1}^{I} c_{k,l,T_i-T_T}\sum_{i=1}^{I}(T_i - T_T)}{\sum_{i=1}^{I}(T_i - T_T)^2 - \frac{1}{I}\left[\sum_{i=1}^{I}(T_i - T_T)\right]^2} \quad (4)$$

and subsequently (knowing the slope $b_{k,l}$) the intercept:

$$c_{k,l,T_T} = \frac{1}{I}\left[\sum_{i=1}^{I} c_{k,l,T_i-T_T} - b_{k,l}\sum_{i=1}^{I}(T_i - T_T)\right] \quad (5)$$

where I is the number of analyses of samples of the same composition at various temperature.

Although the Eq. 3 describes linear dependence of concentration readings on temperature (what empirically is commonly the case), the temperature compensation method can be easily extended to cover non-linear dependences by augmenting Eq. 3 with another term to obtain:

$$c_{k,l,T-T_T} = c_{k,l,T_T} + b_{1,k,l}(T - T_T) + b_{2,k,l}(T - T_T)^2 \quad (6)$$

The regression parameters of Eq. 6 are obtained by Inverse Least Squares (ILS) regression.

Step 1-5: External Validation Experiments and Prediction Calculation

The validation experiments are conducted using sample of the same composition analyzed for all deliberately added bath constituents (K=6) at seven different temperature levels, spanning between 21-27° C., with the $T_T=25.0°$ C. Each component was analyzed using only one, component-specific waveform, therefore L=1. For some components the waveform was repeated M times during the sequence of analyses.

Generally, the voltammetric data for k-th component, l-th waveform, m-th repetition recorded during the time interval $t_{k,l,m}$ of usually ~10 seconds (exceptionally up to 30 seconds) is scaled with the parameters of the training set. The voltammograms for k-th component and l-th waveform use the same regression equation coefficients for concentration for each m-th repetition. The scaled voltammetric data for k-th component, l-th waveform, and m-th repetition is projected on the eigenvector space for k-th component and l-th waveform of the master calibration training set to obtain vector of predicted scores:

$$\hat{s}_{k,l,m} = x_{k,l,m} V_{k,l} \quad (7)$$

The predicted, scaled concentration reading of k-th component, l-th waveform, and m-th repetition are calculated using following expression:

$$\hat{c}_{k,l,m} = \hat{s}_{k,l,m} \beta_{k,l} \quad (8)$$

implementing vector of regression coefficients obtained from the Eq. 2. The predicted concentrations are then rescaled using the scaling parameters of the master calibration. For each k-th component the intelligent averaging is conducted for predicted concentration values for L waveforms and M repetitions.

The numerical results obtained for validation solutions at different temperature are presented below in Table 3. These concentration readings were obtained using the eigenvector space and regression coefficient calculated for the analytical model developed at constant temperature $T_T=25.0°$ C. These readings do not take into account the temperature dependence of the voltammetric signal. Therefore, only the readings at $T_T=25.0°$ C. can be considered as predicted concentrations.

TABLE 3

Bath Component Measurements Without Temperature Compensation Model

| Temperature deg C. | Copper g/l | Acid g/l | Chloride mg/l | Add. 1 ml/l | Add. 2 ml/l | Add. 3 ml/l |
|---|---|---|---|---|---|---|
| 21 | 53.4 | 8.71 | 52.7 | 1.92 | 2.26 | 10.3 |
| 22 | 54.8 | 8.72 | 54.0 | 2.02 | 2.24 | 10.2 |
| 23 | 55.9 | 9.22 | 54.8 | 2.15 | 2.33 | 10.1 |
| 24 | 57.8 | 9.50 | 56.5 | 2.31 | 2.34 | 9.89 |
| 25 | 59.7 | 9.96 | 57.6 | 2.47 | 2.26 | 9.54 |
| 26 | 61.6 | 10.3 | 58.2 | 2.70 | 2.24 | 9.12 |
| 27 | 63.0 | 10.6 | 57.7 | 2.91 | 2.26 | 8.75 |
| Range/Av % | 16.1 | 19.2 | 9.5 | 40.1 | 4.4 | 16.6 |
| RSD % | 6.2 | 7.9 | 3.8 | 15.4 | 1.8 | 6.1 |

For the readings at other-than-$T_T$ temperature, the influence of temperature needs to be compensated employing the Eq. 3. The concentration reading for k-th component, l-waveform, m-th repetition at temperature T, $\hat{c}_{k,l,m,T-T_T}$, is obtained via the Eq. 8. The temperature-effect-compensated concentration reading for k-th component, l-th waveform, m-th repetition is determined by the following expression:

$$\hat{c}_{k,l,m,T_T} = \hat{c}_{k,l,m,T-T_T} b_{k,l}(T-T_T) \quad (9)$$

Table 4 presents the numerical results obtained with the Eq. 9 for the data of Table 3.

TABLE 4

Bath Component Measurements with Temperature Compensation Model

| Temperature deg C. | Copper g/l | Acid g/l | Chloride mg/l | Add. 1 ml/l | Add. 2 ml/l | Add. 3 ml/l |
|---|---|---|---|---|---|---|
| 21 | 60.0 | 10.1 | 56.4 | 2.58 | 2.25 | 9.26 |
| 22 | 59.8 | 9.76 | 56.8 | 2.52 | 2.23 | 9.42 |
| 23 | 59.2 | 9.91 | 56.7 | 2.48 | 2.33 | 9.56 |
| 24 | 59.5 | 9.85 | 57.4 | 2.48 | 2.34 | 9.62 |
| 25 | 59.7 | 9.96 | 57.6 | 2.47 | 2.26 | 9.54 |
| 26 | 60.0 | 9.98 | 57.3 | 2.53 | 2.24 | 9.39 |
| 27 | 59.7 | 9.93 | 55.8 | 2.58 | 2.27 | 9.29 |
| Range/Av % | 1.3 | 3.4 | 3.1 | 4.6 | 4.6 | 3.8 |
| RSD % | 0.5 | 1.1 | 1.1 | 1.9 | 1.8 | 1.5 |

Approach 2: Embedded Temperature Method

Step 2-1: Waveform Development

The waveform development for embedded temperature method is analogous to that of Approach 1 (Step 1-1) with the exception that one more source of variance (apart from varying concentrations of bath constituents), temperature, is embedded into the model. The solutions used for waveform development are composed based on the 2-level, 7-component fractional factorial, resulting in eight composition combinations. The ninth solution investigated is that of target composition with its measurements conducted at the target temperature (see Table 5).

TABLE 5

Waveform Development Training Set with Embedded Temperature

| Sol # | Copper | Acid | Chloride | Suppressor | Accelerator | Leveler | Temp. |
|---|---|---|---|---|---|---|---|
| DT1 | $c_{Cu,T} - \Delta c_{Cu}$ | $c_{Acid,T} - \Delta c_{Acid}$ | $c_{Cl,T} - \Delta c_{Cl}$ | $c_{Supp,T} + \Delta c_{Supp}$ | $c_{Acc,T} + \Delta c_{Acc}$ | $c_{Lev,T} + \Delta c_{Lev}$ | $T_T - \Delta T$ |
| DT2 | $c_{Cu,T} + \Delta c_{Cu}$ | $c_{Acid,T} - \Delta c_{Acid}$ | $c_{Cl,T} - \Delta c_{Cl}$ | $c_{Supp,T} - \Delta c_{Supp}$ | $c_{Acc,T} - \Delta c_{Acc}$ | $c_{Lev,T} + \Delta c_{Lev}$ | $T_T + \Delta T$ |
| DT3 | $c_{Cu,T} - \Delta c_{Cu}$ | $c_{Acid,T} + \Delta c_{Acid}$ | $c_{Cl,T} - \Delta c_{Cl}$ | $c_{Supp,T} - \Delta c_{Supp}$ | $c_{Acc,T} + \Delta c_{Acc}$ | $c_{Lev,T} - \Delta c_{Lev}$ | $T_T + \Delta T$ |
| DT4 | $c_{Cu,T} + \Delta c_{Cu}$ | $c_{Acid,T} + \Delta c_{Acid}$ | $c_{Cl,T} - \Delta c_{Cl}$ | $c_{Supp,T} + \Delta c_{Supp}$ | $c_{Acc,T} - \Delta c_{Acc}$ | $c_{Lev,T} - \Delta c_{Lev}$ | $T_T - \Delta T$ |
| DT5 | $c_{Cu,T} - \Delta c_{Cu}$ | $c_{Acid,T} - \Delta c_{Acid}$ | $c_{Cl,T} + \Delta c_{Cl}$ | $c_{Supp,T} + \Delta c_{Supp}$ | $c_{Acc,T} - \Delta c_{Acc}$ | $c_{Lev,T} - \Delta c_{Lev}$ | $T_T + \Delta T$ |
| DT6 | $c_{Cu,T} + \Delta c_{Cu}$ | $c_{Acid,T} - \Delta c_{Acid}$ | $c_{Cl,T} + \Delta c_{Cl}$ | $c_{Supp,T} - \Delta c_{Supp}$ | $c_{Acc,T} + \Delta c_{Acc}$ | $c_{Lev,T} - \Delta c_{Lev}$ | $T_T - \Delta T$ |
| DT7 | $c_{Cu,T} - \Delta c_{Cu}$ | $c_{Acid,T} + \Delta c_{Acid}$ | $c_{Cl,T} + \Delta c_{Cl}$ | $c_{Supp,T} - \Delta c_{Supp}$ | $c_{Acc,T} - \Delta c_{Acc}$ | $c_{Lev,T} + \Delta c_{Lev}$ | $T_T - \Delta T$ |
| DT8 | $c_{Cu,T} + \Delta c_{Cu}$ | $c_{Acid,T} + \Delta c_{Acid}$ | $c_{Cl,T} + \Delta c_{Cl}$ | $c_{Supp,T} + \Delta c_{Supp}$ | $c_{Acc,T} + \Delta c_{Acc}$ | $c_{Lev,T} + \Delta c_{Lev}$ | $T_T + \Delta T$ |
| DT9 | $c_{Cu,T}$ | $c_{Acid,T}$ | $c_{Cl,T}$ | $c_{Supp,T}$ | $c_{Acc,T}$ | $C_{Lev,T}$ | $T_T$ |

Step 2-2: Master Calibration Training Set

Voltammograms of waveforms developed in Step 2-1 are taken for collection of master calibration training set data, by analyzing 25 solutions composed as a five-level, four-component linear orthogonal array. See Table 6. The temperature is varied and is treated additional, fourth component. All inorganic constituent are held at their target level.

TABLE 6

Master Calibration Training Set with Embedded Temperature

| Sol# | Suppressor | Accelerator | Leveler | Temperature |
|---|---|---|---|---|
| CT1 | $C_{Supp,T} - \Delta C_{Supp}$ | $C_{Acc,T} - \Delta C_{Acc}$ | $C_{Lev,T} - \Delta C_{Lev}$ | $T_T - \Delta T$ |
| CT2 | $C_{Supp,T} - \Delta C_{Supp}$ | $C_{Acc,T} - 0.5\Delta C_{Acc}$ | $C_{Lev,T} - 0.5\Delta C_{Lev}$ | $T_T - 0.5\Delta T$ |
| CT3 | $C_{Supp,T} - \Delta C_{Supp}$ | $C_{Acc,T}$ | $C_{Lev,T}$ | $T_T$ |
| CT4 | $C_{Supp,T} - \Delta C_{Supp}$ | $C_{Acc,T} + 0.5\Delta C_{Acc}$ | $C_{Lev,T} + 0.5\Delta C_{Lev}$ | $T_T + 0.5\Delta T$ |
| CT5 | $C_{Supp,T} - \Delta C_{Supp}$ | $C_{Acc,T} + \Delta C_{Acc}$ | $C_{Lev,T} + \Delta C_{Lev}$ | $T_T + \Delta T$ |
| CT6 | $C_{Supp,T} - 0.5\Delta C_{Supp}$ | $C_{Acc,T} - \Delta C_{Acc}$ | $C_{Lev,T} - 0.5\Delta C_{Lev}$ | $T_T$ |
| CT7 | $C_{Supp,T} - 0.5\Delta C_{Supp}$ | $C_{Acc,T} - 0.5\Delta C_{Acc}$ | $C_{Lev,T}$ | $T_T + 0.5\Delta T$ |
| CT8 | $C_{Supp,T} - 0.5\Delta C_{Supp}$ | $C_{Acc,T}$ | $C_{Lev,T} + 0.5\Delta C_{Lev}$ | $T_T + \Delta T$ |
| CT9 | $C_{Supp,T} - 0.5\Delta C_{Supp}$ | $C_{Acc,T} + 0.5\Delta C_{Acc}$ | $C_{Lev,T} + \Delta C_{Lev}$ | $T_T - \Delta T$ |

TABLE 6-continued

Master Calibration Training Set with Embedded Temperature

| Sol# | Suppressor | Accelerator | Leveler | Temperature |
| --- | --- | --- | --- | --- |
| CT10 | $C_{Supp,T} - 0.5\Delta C_{Supp}$ | $C_{Acc,T} + \Delta C_{Acc}$ | $C_{Lev,T} - \Delta C_{Lev}$ | $T_T - 0.5\Delta T$ |
| CT11 | $C_{Supp,T}$ | $C_{Acc,T} - \Delta C_{Acc}$ | $C_{Lev,T}$ | $T_T - \Delta T$ |
| CT12 | $C_{Supp,T}$ | $C_{Acc,T} - 0.5\Delta C_{Acc}$ | $C_{Lev,T} + 0.5\Delta C_{Lev}$ | $T_T - \Delta T$ |
| CT13 | $C_{Supp,T}$ | $C_{Acc,T}$ | $C_{Lev,T} + \Delta C_{Lev}$ | $T_T - 0.5\Delta T$ |
| CT14 | $C_{Supp,T}$ | $C_{Acc,T} + 0.5\Delta C_{Acc}$ | $C_{Lev,T} \Delta C_{Lev}$ | $T_T$ |
| CT15 | $C_{Supp,T}$ | $C_{Acc,T} + \Delta C_{Acc}$ | $C_{Lev,T} - 0.5\Delta C_{Lev}$ | $T_T + 0.5\Delta T$ |
| CT16 | $C_{Supp,T} + 0.5\Delta C_{Supp}$ | $C_{Acc,T} - \Delta C_{Acc}$ | $C_{Lev,T} + 0.5\Delta C_{Lev}$ | $T_T - 0.5\Delta T$ |
| CT17 | $C_{Supp,T} + 0.5\Delta C_{Supp}$ | $C_{Acc,T} - 0.5\Delta C_{Acc}$ | $C_{Lev,T} + \Delta C_{Lev}$ | $T_T$ |
| CT18 | $C_{Supp,T} + 0.5\Delta C_{Supp}$ | $C_{Acc,T}$ | $C_{Lev,T} - \Delta C_{Lev}$ | $T_T + 0.5\Delta T$ |
| CT19 | $C_{Supp,T} + 0.5\Delta C_{Supp}$ | $C_{Acc,T} + 0.5\Delta C_{Acc}$ | $C_{Lev,T} - 0.5\Delta C_{Lev}$ | $T_T + \Delta T$ |
| CT20 | $C_{Supp,T} + 0.5\Delta C_{Supp}$ | $C_{Acc,T} + \Delta C_{Acc}$ | $C_{Lev,T}$ | $T_T - \Delta T$ |
| CT21 | $C_{Supp,T} + \Delta C_{Supp}$ | $C_{Acc,T} - \Delta C_{Acc}$ | $C_{Lev,T} + \Delta C_{Lev}$ | $T_T + 0.5\Delta T$ |
| CT22 | $C_{Supp,T} + \Delta C_{Supp}$ | $C_{Acc,T} - 0.5\Delta C_{Acc}$ | $C_{Lev,T} \Delta C_{Lev}$ | $T_T + \Delta T$ |
| CT23 | $C_{Supp,T} + \Delta C_{Supp}$ | $C_{Acc,T}$ | $C_{Lev,T} - 0.5\Delta C_{Lev}$ | $T_T - \Delta T$ |
| CT24 | $C_{Supp,T} + \Delta C_{Supp}$ | $C_{Acc,T} + 0.5\Delta C_{Acc}$ | $C_{Lev,T}$ | $T_T - 0.5\Delta T$ |
| CT25 | $C_{Supp,T} + \Delta C_{Supp}$ | $C_{Acc/T} + \Delta C_{Acc}$ | $C_{Lev,T} + 0.5\Delta C_{Lev}$ | $T_T$ |

Optionally, the variance inflicted by changing concentrations of inorganic bath constituents can be incorporated into the master calibration training set by augmenting the data collected for 27 solutions of composition corresponding to three-level, seven-component linear orthogonal array as outlined in the Table 7.

ing voltammetric data. Similarly to dual-regression method, the initial step of the embedded temperature method is the PCA decomposition using number of factors of F as described by the Eq. 1. The resultant matrix of scores S of dimensions (N×F) is subsequently appended by the autoscaled column vector of temperature values t of size

TABLE 7

Additional Master Calibration Training Set with Varied Concentrations of All Constituent and Embedded Temperature

| Sol # | Copper | Acid | Chloride | Suppressor | Accelerator | Leveler | Temp. |
| --- | --- | --- | --- | --- | --- | --- | --- |
| CO1 | $c_{Cu,T} - \Delta c_{Cu}$ | $c_{Acid,T} - \Delta c_{Acid}$ | $c_{Cl,T} - \Delta c_{Cl}$ | $c_{Supp,T} - \Delta c_{Supp}$ | $c_{Acc,T} - \Delta c_{Acc}$ | $c_{Lev,T} - \Delta c_{Lev}$ | $T_T - \Delta T$ |
| CO2 | $c_{Cu,T} - \Delta c_{Cu}$ | $c_{Acid,T} - \Delta c_{Acid}$ | $c_{Cl,T} - \Delta c_{Cl}$ | $c_{Supp,T} - \Delta c_{Supp}$ | $c_{Acc,T}$ | $c_{Lev,T}$ | $T_T$ |
| CO3 | $c_{Cu,T} - \Delta c_{Cu}$ | $c_{Acid,T} - \Delta c_{Acid}$ | $c_{Cl,T} - \Delta c_{Cl}$ | $c_{Supp,T} - \Delta c_{Supp}$ | $c_{Acc,T} + \Delta c_{Acc}$ | $c_{Lev,T} + \Delta c_{Lev}$ | $T_T + \Delta T$ |
| CO4 | $c_{Cu,T} - \Delta c_{Cu}$ | $c_{Acid,T}$ | $c_{Cl,T}$ | $c_{Supp,T}$ | $c_{Acc,T} - \Delta c_{Acc}$ | $c_{Lev,T} - \Delta c_{Lev}$ | $T_T - \Delta T$ |
| CO5 | $c_{Cu,T} - \Delta c_{Cu}$ | $c_{Acid,T}$ | $c_{Cl,T}$ | $c_{Supp,T}$ | $c_{Acc,T}$ | $c_{Lev,T}$ | $T_T$ |
| CO6 | $c_{Cu,T} - \Delta c_{Cu}$ | $c_{Acid,T}$ | $c_{Cl,T}$ | $c_{Supp,T}$ | $c_{Acc,T} + \Delta c_{Acc}$ | $c_{Lev,T} + \Delta c_{Lev}$ | $T_T + \Delta T$ |
| CO7 | $c_{Cu,T} - \Delta c_{Cu}$ | $c_{Acid,T} + \Delta c_{Acid}$ | $c_{Cl,T} + \Delta c_{Cl}$ | $c_{Supp,T} + \Delta c_{Supp}$ | $c_{Acc,T} - \Delta c_{Acc}$ | $c_{Lev,T} - \Delta c_{Lev}$ | $T_T - \Delta T$ |
| CO8 | $c_{Cu,T} - \Delta c_{Cu}$ | $c_{Acid,T} + \Delta c_{Acid}$ | $c_{Cl,T} + \Delta c_{Cl}$ | $c_{Supp,T} + \Delta c_{Supp}$ | $c_{Acc,T}$ | $c_{Lev,T}$ | $T_T$ |
| CO9 | $c_{Cu,T} - \Delta c_{Cu}$ | $c_{Acid,T} + \Delta c_{Acid}$ | $c_{Cl,T} + \Delta c_{Cl}$ | $c_{Supp,T} + \Delta c_{Supp}$ | $c_{Acc,T} + \Delta c_{Acc}$ | $c_{Lev,T} + \Delta c_{Lev}$ | $T_T + \Delta T$ |
| CO10 | $c_{Cu,T}$ | $c_{Acid,T} - \Delta c_{Acid}$ | $c_{Cl,T}$ | $c_{Supp,T} + \Delta c_{Supp}$ | $c_{Acc,T} - \Delta c_{Acc}$ | $c_{Lev,T}$ | $T_T + \Delta T$ |
| CO11 | $c_{Cu,T}$ | $c_{Acid,T} - \Delta c_{Acid}$ | $c_{Cl,T}$ | $c_{Supp,T} + \Delta c_{Supp}$ | $c_{Acc,T}$ | $c_{Lev,T} + \Delta c_{Lev}$ | $T_T - \Delta T$ |
| CO12 | $c_{Cu,T}$ | $c_{Acid,T} - \Delta c_{Acid}$ | $c_{Cl,T}$ | $c_{Supp,T} + \Delta c_{Supp}$ | $c_{Acc,T} + \Delta c_{Acc}$ | $c_{Lev,T} - \Delta c_{Lev}$ | $T_T$ |
| CO13 | $c_{Cu,T}$ | $c_{Acid,T}$ | $c_{Cl,T} + \Delta c_{Cl}$ | $c_{Supp,T} - \Delta c_{Supp}$ | $c_{Acc,T} - \Delta c_{Acc}$ | $c_{Lev,T}$ | $T_T + \Delta T$ |
| CO14 | $c_{Cu,T}$ | $c_{Acid,T}$ | $c_{Cl,T} + \Delta c_{Cl}$ | $c_{Supp,T} - \Delta c_{Supp}$ | $c_{Acc,T}$ | $c_{Lev,T} + \Delta c_{Lev}$ | $T_T - \Delta T$ |
| CO15 | $c_{Cu,T}$ | $c_{Acid,T}$ | $c_{Cl,T} + \Delta c_{Cl}$ | $c_{Supp,T} - \Delta c_{Supp}$ | $c_{Acc,T} + \Delta c_{Acc}$ | $c_{Lev,T} - \Delta c_{Lev}$ | $T_T$ |
| CO16 | $c_{Cu,T}$ | $c_{Acid,T} + \Delta c_{Acid}$ | $c_{Cl,T} - \Delta c_{Cl}$ | $c_{Supp,T}$ | $c_{Acc,T} - \Delta c_{Acc}$ | $c_{Lev,T}$ | $T_T + \Delta T$ |
| CO17 | $c_{Cu,T}$ | $c_{Acid,T} + \Delta c_{Acid}$ | $c_{Cl,T} - \Delta c_{Cl}$ | $c_{Supp,T}$ | $c_{Acc,T}$ | $c_{Lev,T} + \Delta c_{Lev}$ | $T_T - \Delta T$ |
| CO18 | $c_{Cu,T}$ | $c_{Acid,T} + \Delta c_{Acid}$ | $c_{Cl,T} - \Delta c_{Cl}$ | $c_{Supp,T}$ | $c_{Acc,T} + \Delta c_{Acc}$ | $c_{Lev,T} - \Delta c_{Lev}$ | $T_T$ |
| CO19 | $c_{Cu,T} + \Delta c_{Cu}$ | $c_{Acid,T} - \Delta c_{Acid}$ | $c_{Cl,T} + \Delta c_{Cl}$ | $c_{Supp,T}$ | $c_{Acc,T} - \Delta c_{Acc}$ | $c_{Lev,T} + \Delta c_{Lev}$ | $T_T$ |
| CO20 | $c_{Cu,T} + \Delta c_{Cu}$ | $c_{Acid,T} - \Delta c_{Acid}$ | $c_{Cl,T} + \Delta c_{Cl}$ | $c_{Supp,T}$ | $c_{Acc,T}$ | $c_{Lev,T} - \Delta c_{Lev}$ | $T_T + \Delta T$ |
| CO21 | $c_{Cu,T} + \Delta c_{Cu}$ | $c_{Acid,T} - \Delta c_{Acid}$ | $c_{Cl,T} + \Delta c_{Cl}$ | $c_{Supp,T}$ | $c_{Acc,T} + \Delta c_{Acc}$ | $c_{Lev,T}$ | $T_T - \Delta T$ |
| CO22 | $c_{Cu,T} + \Delta c_{Cu}$ | $c_{Acid,T}$ | $c_{Cl,T} - \Delta c_{Cl}$ | $c_{Supp,T} + \Delta c_{Supp}$ | $c_{Acc,T} - \Delta c_{Acc}$ | $c_{Lev,T} + \Delta c_{Lev}$ | $T_T$ |
| CO23 | $c_{Cu,T} + \Delta c_{Cu}$ | $c_{Acid,T}$ | $c_{Cl,T} - \Delta c_{Cl}$ | $c_{Supp,T} + \Delta c_{Supp}$ | $c_{Acc,T}$ | $c_{Lev,T} - \Delta c_{Lev}$ | $T_T + \Delta T$ |
| CO24 | $c_{Cu,T} + \Delta c_{Cu}$ | $c_{Acid,T}$ | $c_{Cl,T} - \Delta c_{Cl}$ | $c_{Supp,T} + \Delta c_{Supp}$ | $c_{Acc,T} + \Delta c_{Acc}$ | $c_{Lev,T}$ | $T_T - \Delta T$ |
| CO25 | $c_{Cu,T} + \Delta c_{Cu}$ | $c_{Acid,T} + \Delta c_{Acid}$ | $c_{Cl,T}$ | $c_{Supp,T} - \Delta c_{Supp}$ | $c_{Acc,T} - \Delta c_{Acc}$ | $c_{Lev,T} + \Delta c_{Lev}$ | $T_T$ |
| CO26 | $c_{Cu,T} + \Delta c_{Cu}$ | $c_{Acid,T} + \Delta c_{Acid}$ | $c_{Cl,T}$ | $c_{Supp,T} - \Delta c_{Supp}$ | $c_{Acc,T}$ | $c_{Lev,T} - \Delta c_{Lev}$ | $T_T + \Delta T$ |
| CO27 | $c_{Cu,T} - \Delta c_{Cu}$ | $c_{Acid,T} + \Delta c_{Acid}$ | $c_{Cl,T}$ | $c_{Supp,T} - \Delta c_{Supp}$ | $c_{Acc,T} + \Delta c_{Acc}$ | $c_{Lev,T}$ | $T_T - \Delta T$ |

Step 2-3: Consolidated Regression Calculation

The consolidated regression equation is calculated with model-embedded variance inflicted by temperature changes. The regression is calculated for a portion of each l-th waveform for k-th component using pretreated by autoscal- (N×1) to form the matrix of temperature-augmented scores D of the size (N×(F+1)):

$$D_{k,l} = [S_{k,l} t_{k,l}] \qquad (10)$$

The matrix of temperature-augmented PCA scores, D, is regressed linearly against the vector of concentrations by means of Inverse Least Squares (ILS) obtaining. For each k-th component and l-th waveform the corresponding vector of F+1 regression equation coefficients are calculated:

$$\gamma_{k,l} = (D_{k,l}{}^T D_{k,l})^{-1} D_{k,l}{}^T c_k \quad (11)$$

Step 2-4: External Validation Set and Concentration Prediction

The consolidated-regression analytical model developed in Step 2-3 is subsequently validated by collecting and analyzing voltammetric data for 16 solutions composed as a four-level, four-component linear orthogonal array (see Table 8). The temperature is varied and is treated additional, fourth component. All inorganic constituent are held at their target level.

The emphasis was put on using in the validation training set concentration values (and temperature values) different from that of Tables 6 and 7. Of course, the concentration and temperature values of Table 8 are within calibration concentration ranges of master calibration training set.

Step 2-5: Exemplary External Validation Experiments and Prediction Calculation The validation experiments are conducted for the bath whose specific target level concentrations were following: $c_{Supp,T}=8.5$ ml/l, $c_{Acc,T}=7.5$ ml/l, and $c_{Lev,T}=1.63$ ml/l and the target temperature $T_T=25.0°$ C. For the waveform development (Table 5) and master calibration training set (Table 6) experiments and subsequent regression calculations the concentrations were varied as determined by following parameters: $\Delta C_{Supp}=3.5$ ml/l, $\Delta c_{Acc}=2.5$ ml/l, and, $\Delta c_{Lev}=0.88$ ml/l. The temperature was varied symmetrically around its target values based on $\Delta T=3.0°$ C. By implementing these specific values of concentration and temperature parameters into the formulas of Table 8 one obtains the following compositions of exemplary external validation set outlined in Table 9.

TABLE 8

External Validation Training Set with Embedded Temperature Variance

| Sol # | Suppressor | Accelerator | Leveler | Temperature |
|---|---|---|---|---|
| VT1 | $C_{Supp,T} - 0.75\Delta C_{Supp}$ | $C_{Acc,T} - 0.75\Delta C_{Acc}$ | $C_{Lev,T} - 0.75\Delta C_{Lev}$ | $T_T - 0.75\Delta T$ |
| VT2 | $C_{Supp,T} - 0.75\Delta C_{Supp}$ | $C_{Acc,T} - 0.25\Delta C_{Acc}$ | $C_{Lev,T} - 0.25\Delta C_{Lev}$ | $T_T - 0.25\Delta T$ |
| VT3 | $C_{Supp,T} - 0.75\Delta C_{Supp}$ | $C_{Acc,T} - 0.25\Delta C_{Acc}$ | $C_{Lev,T} + 0.25\Delta C_{Lev}$ | $T_T + 0.25\Delta T$ |
| VT4 | $C_{Supp,T} - 0.75\Delta C_{Supp}$ | $C_{Acc,T} + 0.75\Delta C_{Acc}$ | $C_{Lev,T} + 0.75\Delta C_{Lev}$ | $T_T + 0.75\Delta T$ |
| VT5 | $C_{Supp,T} - 0.25\Delta C_{Supp}$ | $C_{Acc,T} - 0.75\Delta C_{Acc}$ | $C_{Lev,T} - 0.25\Delta C_{Lev}$ | $T_T + 0.25\Delta T$ |
| VT6 | $C_{Supp,T} - 0.25\Delta C_{Supp}$ | $C_{Acc,T} - 0.25\Delta C_{Acc}$ | $C_{Lev,T} - 0.75\Delta C_{Lev}$ | $T_T + 0.75\Delta T$ |
| VT7 | $C_{Supp,T} - 0.25\Delta C_{Supp}$ | $C_{Acc,T} + 0.25\Delta C_{Acc}$ | $C_{Lev,T} + 0.75\Delta C_{Lev}$ | $T_T - 0.75\Delta T$ |
| VT8 | $C_{Supp,T} - 0.25\Delta C_{Supp}$ | $C_{Acc,T} + 0.75\Delta C_{Acc}$ | $C_{Lev,T} + 0.25\Delta C_{Lev}$ | $T_T - 0.25\Delta T$ |
| VT9 | $C_{Supp,T} + 0.25\Delta C_{Supp}$ | $C_{Acc,T} - 0.75\Delta C_{Acc}$ | $C_{Lev,T} + 0.25\Delta C_{Lev}$ | $T_T + 0.75\Delta T$ |
| VT10 | $C_{Supp,T} + 0.25\Delta C_{Supp}$ | $C_{Acc,T} - 0.25\Delta C_{Acc}$ | $C_{Lev,T} + 0.75\Delta C_{Lev}$ | $T_T + 0.25\Delta T$ |
| VT11 | $C_{Supp,T} + 0.25\Delta C_{Supp}$ | $C_{Acc,T} + 0.25\Delta C_{Acc}$ | $C_{Lev,T} - 0.75\Delta C_{Lev}$ | $T_T - 0.25\Delta T$ |
| VT12 | $C_{Supp,T} + 0.25\Delta C_{Supp}$ | $C_{Acc,T} + 0.75\Delta C_{Acc}$ | $C_{Lev,T} - 0.25\Delta C_{Lev}$ | $T_T - 0.75\Delta T$ |
| VT13 | $C_{Supp,T} + 0.75\Delta C_{Supp}$ | $C_{Acc,T} - 0.75\Delta C_{Acc}$ | $C_{Lev,T} + 0.75\Delta C_{Lev}$ | $T_T - 0.25\Delta T$ |
| VT14 | $C_{Supp,T} + 0.75\Delta C_{Supp}$ | $C_{Acc,T} - 0.25\Delta C_{Acc}$ | $C_{Lev,T} + 0.25\Delta C_{Lev}$ | $T_T - 0.75\Delta T$ |
| VT15 | $C_{Supp,T} + 0.75\Delta C_{Supp}$ | $C_{Acc,T} + 0.25\Delta C_{Acc}$ | $C_{Lev,T} - 0.25\Delta C_{Lev}$ | $T_T + 0.75\Delta T$ |
| VT16 | $C_{Supp,T} + 0.75\Delta C_{Supp}$ | $C_{Acc,T} + 0.75\Delta C_{Acc}$ | $C_{Lev,T} - 0.75\Delta C_{Lev}$ | $T_T + 0.25\Delta T$ |

Analogously to the dual-regression approach, also for the embedded temperature model the scaled voltammetric data for k-th component, l-th waveform, and m-th repetition is projected on the eigenvector space for k-th component and l-th waveform of the master calibration training set to obtain vector of predicted scores: via Equation 7. The vector of projected scores is subsequently augmented by the scaled temperature value measured during recording of the l-th voltammetric waveform for k-th component and m-th repetition:

$$\hat{d}_{k,l,m} = [\hat{s}_{k,l,m} \hat{t}_{k,l,m}] \quad (12)$$

The temperature value is scaled using the parameters of the master calibration training set.

The predicted, scaled concentration reading of k-th component, l-th waveform, and m-th repetition is calculated using consolidated regression coefficient of Equation 11 and implementing them to the following expression:

$$\hat{c}_{k,l,m} = \hat{d}_{k,l,m} \gamma_{k,l} \quad (13)$$

Finally, the predicted concentration values expressed in units of ml/l are obtained by rescaling of the outcome of the Eq. 13 using the scaling parameters of the master calibration training set.

TABLE 9

Exemplary external validation training set with embedded temperature variance

| Solution # | Analysis # | Suppressor ml/l | Accelerator ml/l | Leveler ml/l | Temperature deg C. |
|---|---|---|---|---|---|
| VT1 | 1, 2 | 5.88 | 5.63 | 0.97 | 22.8 |
| VT2 | 3, 4 | 5.88 | 6.88 | 1.41 | 24.3 |
| VT3 | 5, 6 | 5.88 | 8.13 | 1.84 | 25.8 |
| VT4 | 7, 8 | 5.88 | 9.38 | 2.28 | 27.3 |
| VT5 | 9, 10 | 7.63 | 5.63 | 1.41 | 25.8 |
| VT6 | 11, 12 | 7.63 | 6.88 | 0.97 | 27.3 |
| VT7 | 13, 14 | 7.63 | 8.13 | 2.28 | 22.8 |
| VT8 | 15, 16 | 7.63 | 9.38 | 1.84 | 24.3 |
| VT9 | 17, 18 | 9.38 | 5.63 | 1.84 | 27.3 |
| VT10 | 19, 20 | 9.38 | 6.88 | 2.28 | 25.8 |
| VT11 | 21, 22 | 9.38 | 8.13 | 0.97 | 24.3 |
| VT12 | 23, 24 | 9.38 | 9.38 | 1.41 | 22.8 |
| VT13 | 25, 26 | 11.13 | 5.63 | 2.28 | 24.3 |
| VT14 | 27, 28 | 11.13 | 6.88 | 1.84 | 22.8 |
| VT15 | 29, 30 | 11.13 | 8.13 | 1.41 | 27.3 |
| VT16 | 31, 32 | 11.13 | 9.38 | 0.97 | 25.8 |

Figure 3:
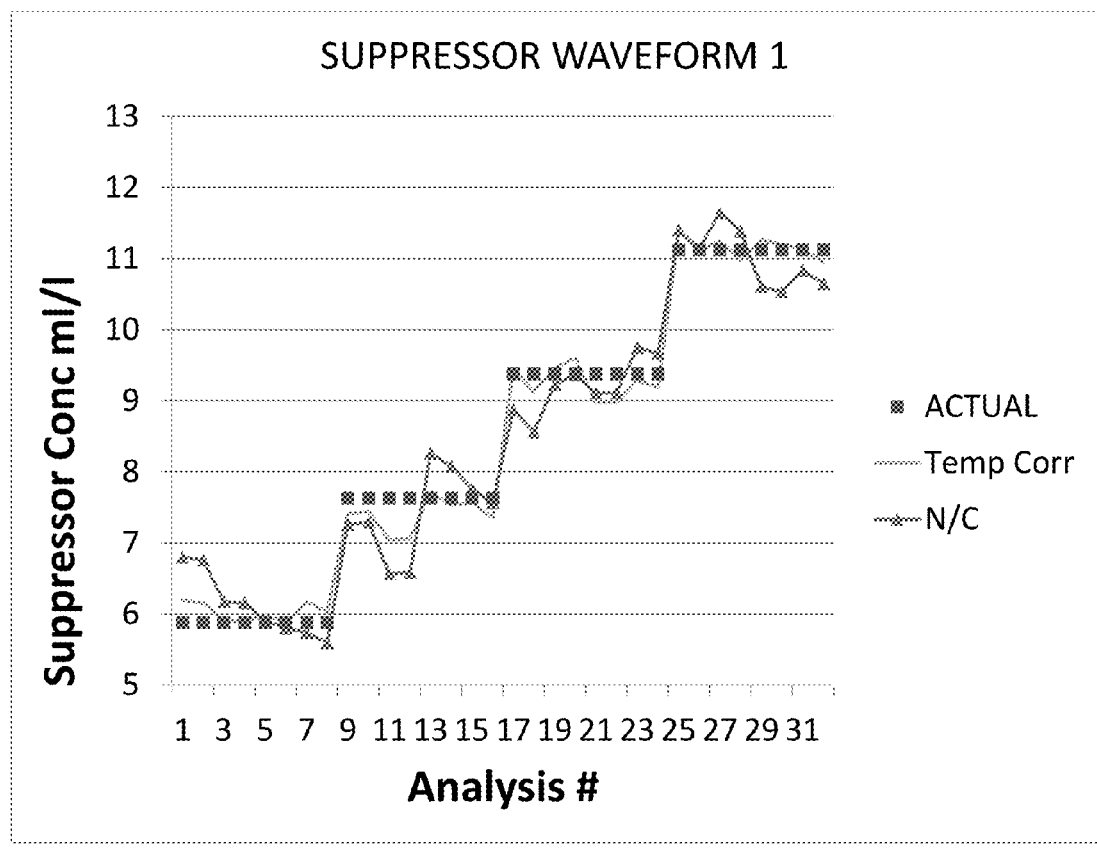
FIG. 3 is a graphic representation of the comparison of validation results for the solutions of Table 9 obtained with and without temperature compensation for waveform 1 (l=1) for suppressor (k=1).
Figure 4:
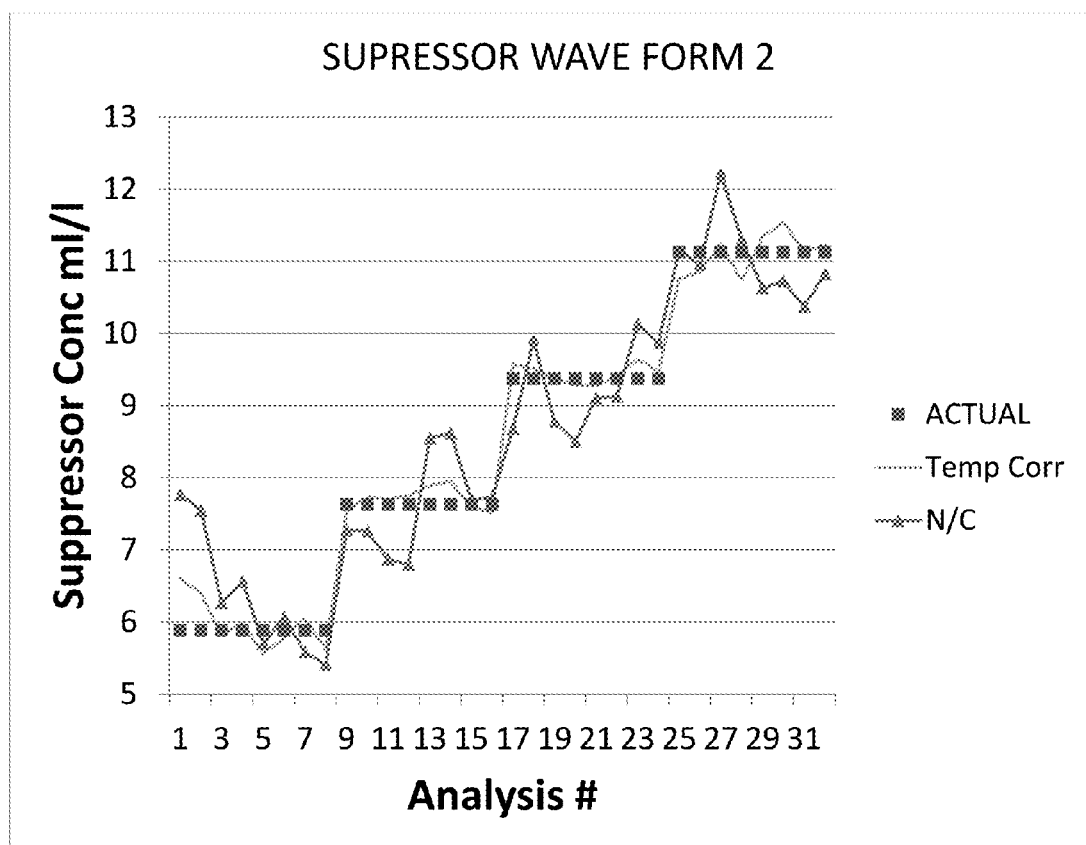
FIG. 4 is a graphic representation of the comparison of validation results for the solutions of Table 9 obtained with and without temperature compensation for waveform 2 (l=2) for suppressor (k=1).
Figure 5:
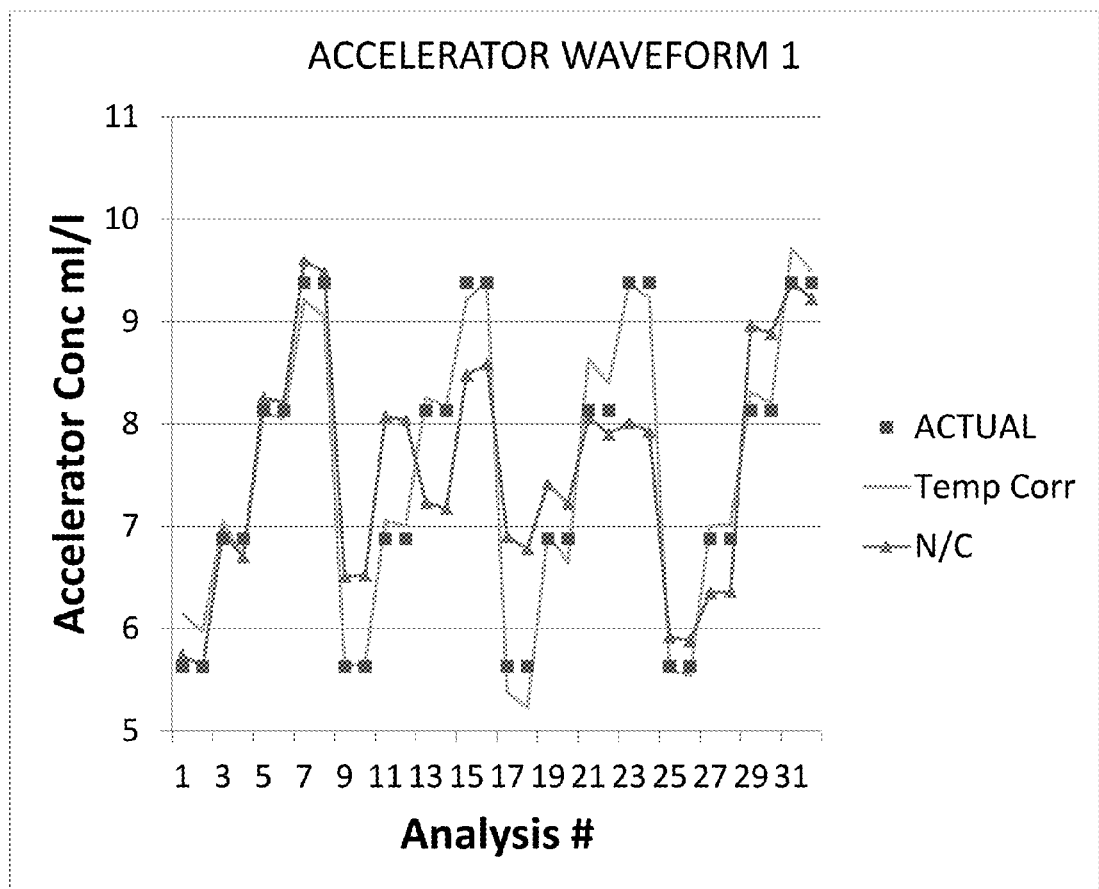
FIG. 5 is a graphic representation of the comparison of validation results for the solutions of Table 9, obtained with and without temperature compensation for waveform 1 (l=1) for accelerator (k=2).
Figure 6:
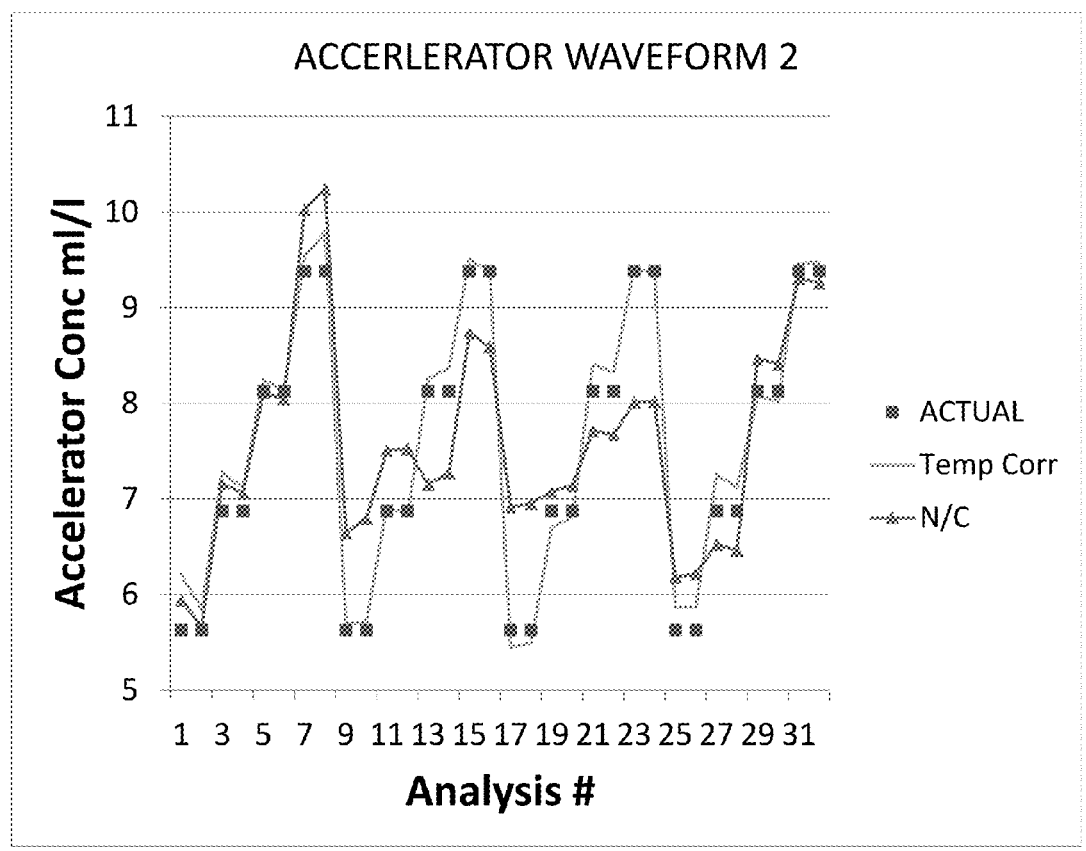
FIG. 6 is a graphic representation of the comparison of validation results for solutions of Table 9 obtained with and without temperature compensation for waveform 2 (l=2) for accelerator (k=2).

Each of 16 solutions VT1 to VT16 of the composition presented in Table 9 was analyzed in duplicate resulting in the total number of analyses of $N_V=32$. Each of the bath components was analyzed using voltammograms of different waveforms in order to gather analytical information from different physicochemical perspective. Some selected, exemplary numerical data obtained for validatory experiments for two different waveforms developed for suppressor (component index k=1) analysis and two other waveforms developed specifically for accelerator (component index k=2) concentration determination are presented in FIGS. 3, 4 and 5, 6, respectively. Each of FIGS. 3-6 present comparative results for actual concentration values, predicted concentration values obtained without temperature correction (via regression equation Eq. 2), and with embedded temperature compensation (consolidated regression equation Eq. 11).

It needs to be emphasized at this point that each bath constituent requires its own set of custom-developed, component-specific waveforms (voltammetric routines) producing current response changing linearly with concentration changes of component of interest while being independent of all other variances (matrix effects, concentration variation due to other bath constituents). Therefore, for instance the waveform of index j=1 for suppressor (of component index k=1) is a different voltammetric routine than the waveform of index j=1 for accelerator (k=2).

The visual analysis of data in FIGS. 3-6 demonstrates substantial improvement of accuracy of prediction and correlation of predicted-to-actual concentration values by introduction of temperature compensation (using the embedded temperature model) as compared to results obtained without temperature correction. The conclusions of visual observation are supported by the quantitative assessment of data using as parameters coefficient of determination (squared correlation coefficient, $R^2$) and Root Mean Squared Error of Prediction (RMSEP) calculated for validation set data with and without temperature compensation for some selected for an example in Table 10:

TABLE 10

$R^2$ and RMSEP Calculated for Exemplary Analyses of Validation Set Data With and Without Temperature Compensation Using Temperature Embedded Model

| Component | k | l | $N_V$ | J | m | F | $R^2$ no T comp | $R^2$ T comp | RMSEP no T comp | RMSEP T comp |
|---|---|---|---|---|---|---|---|---|---|---|
| Supp | 1 | 1 | 32 | 23 | 1 | 1 | 0.9386 | 0.9859 | 0.4892 | 0.2370 |
| Supp | 1 | 2 | 32 | 23 | 1 | 2 | 0.8717 | 0.9845 | 0.7046 | 0.2494 |
| Acc | 2 | 1 | 32 | 56 | 1 | 1 | 0.7322 | 0.9769 | 0.7283 | 0.2165 |
| Acc | 2 | 2 | 32 | 26 | 1 | 3 | 0.7507 | 0.9839 | 0.7094 | 0.2131 |

The RMSEP is defined by the following formula for m-th repetition of j-th waveform within the sequence of RTA scans for k-th component during i-th analysis out of the total of $N_v$ of external validation set:

$$RMSEP_{k,j,m} = \sqrt{\frac{\sum_{i=1}^{N_V}(\hat{c}_{k,l,m,i} - c_{k,i})^2}{N_V}} \quad (14)$$

The numerical results in Table 10 demonstrate significant improvement of values of critical parameters, $R^2$ and RMSEP, used for assessment of predictive performance of analytical models by incorporation of temperature compensation embedded in the model as compared to that of no temperature compensation.

We claim:

1. A process for creating a calibration data set to predict the amount of deliberately added constituents in an electrolyte solution at various temperatures, the process comprising:
    (a) obtaining a sample set, wherein each sample in the set comprises an electrolyte solution of known composition;
    (b) obtaining an electroanalytical response for each sample in the sample set to produce an electroanalytical response data set at various temperatures in a preselected range of low to high temperature limits;
    (c) obtaining a training set that comprises the sample set and the corresponding electroanalytical response data set at various temperatures in the preselected range of low to high temperature limits including the target temperature;
    (d) preprocessing the training set;
    (e) determining the calibration range;
    (f) detecting and eliminating outliers from the response data set;
    (g) determining the optimal number of factors;
    (h) detecting and eliminating outliers within training set;
    (i) analyzing the training set using multivariate regression to produce a regression set with embedded temperature compensation of temperature variation in the temperature of the electrolyte solution;
    (j) cross validating a subset of the training set using multivariate regression to compensate for the effect of temperature on electroanalytical response, which produces a regression set with temperature compensation; and
    (k) validating the regression set with temperature compensation to produce a predictive set for a predictive calibration model for various temperatures in the preselected range low to high limits.

2. The process according to claim 1 wherein the electrolyte solution is an electroplating bath.

3. The process of claim 2 wherein the electroplating bath comprises a plating bath of one or more metals selected from the group consisting of Cu, Sn, Pb, Zn, Ni, Ag, Cd, Co, Cr, and/or their alloys.

4. The process according to claim 1 wherein the electrolyte solution is an electroless plating bath.

5. The process of claim 4 wherein the electroless plating bath comprises an autocatalytic plating bath of one or more metals selected from the group consisting of Cu, Sn, Pb, Ni, Ag, Au, and/or their alloys or an immersion plating bath of one or more metals selected from the group consisting of Cu, Sn, Pb, Ni, Ag, Au and/or their alloys.

6. The process according to claim 1 wherein the electroanalytical response of step (b) is obtained by a method selected from the group consisting of DC Voltammetry, Normal Pulse Voltammetry, Reverse Pulse Voltammetry, Differential Pulse Voltammetry, Square Wave Voltammetry, AC Voltammetry, MultiFrequency AC Voltammetry, Chronoamperometry, Chronopotentiometry, Electrochemical Impedance Spectroscopy, Dynamic Electrochemical Impedance Spectroscopy, a Polarographic technique, and a combination of any two or more of the foregoing techniques.

7. The process of claim 6 wherein the DC Voltammetry technique is selected from the group consisting of DC Cyclic Voltammetry, DC Linear Scan Voltammetry, DC Anodic Stripping Voltammetry, DC Cathodic Stripping Voltammetry, DC Adsorptive Stripping Voltammetry, and DC Cyclic Voltammetric Stripping, and DC Staircase Voltammetry.

8. The process according to claim 1 wherein the electroanalytical response of step (b) comprises a plurality of data points.

9. The process according to claim 1 wherein the electroanalytical response of step (b) is a combination of one or more portions of a complete electroanalytical response.

10. The process according to claim 1 wherein the electroanalytical response of step (b) comprises a combination of one or more portions of independent electroanalytical responses.

11. The process according to claim 1 wherein step (d) comprises autoscaling the data to unit variance.

12. The process according to claim 1 wherein step (e) comprises the steps of:
 a) analyzing the data set using correlation coefficient calculations based on the least squares regression;
 b) analyzing the data set using SIMCA based calculations of modeling power; and
 c) analyzing the data set using a product of the correlation coefficient and the modeling power.

13. The process according to claim 1 wherein step (f) comprises analyzing the data set using a techniques selected from the group consisting of principle component analysis, Mahalanobis distance, Mahalanobis distance coupled with principal component analysis, Mahalanobis distance coupled with said principal component analysis with Q residuals, SIMCA, and PRESS.

14. The process according to claim 13 wherein the PRESS analysis is based on PCR, HPCR, CPCR, PARAFAC/ILS calculations or on PLS, HPLS, MBPLS, NPLS calculations.

15. The process according to claim 1 wherein step (h) comprises analyzing the data using a technique selected from the group consisting of $F^c$ ratio analysis, Studentized concentration residuals analysis, leverages analysis, and Studentized concentration residuals analysis coupled with leverages analysis.

16. The process according to claim 1 wherein step (i) comprises analyzing the data using PLS, HPLS, MBPLS, NPLS or using PCR, HPCR, CPCR, PARAFAC/ILS.

17. A process for predicting the concentration of deliberately added constituents in an electrolyte solution comprising:
 (a) generating a predictive data set by:
  (1) obtaining a sample set, wherein each sample in the sample set comprises an electrolyte solution of known composition;
  (2) obtaining an electroanalytical response for each sample in the sample set to produce an electroanalytical response data set for various temperatures in a preselected low to high limit range;
  (3) obtaining a training set that comprises the sample set and the corresponding electroanalytical response data set for various temperatures in the preselected low to high limit range;
  (4) analyzing the training set using decomposition and multivariate regression method to produce a regression set with embedded temperature compensation of temperature variation in the temperature of the electrolyte solution; and
  (5) validating the training data set to produce the predictive data set for a predictive calibration model for various temperatures in the preselected range of low to high limits and building such a calibration model;
 (b) using the predictive data set produced in (a) to predict the concentration of deliberately added constituents at various temperature levels in a preselected low to high limit range by:
  (1) obtaining an unknown sample set, wherein each unknown sample in said unknown sample set contains an electrolyte solution;
  (2) obtaining an electroanalytical response at various temperature levels in a preselected low to high limit range for each unknown sample to produce an produce an electroanalytical response data set;
  (3) preprocessing the electroanalytical response data set; and
  (4) applying the predictive calibration model with compensation for the effect of temperature on electroanalytical response in order to predict the concentration of deliberately added components in each sample.

* * * * *